(12) United States Patent
Hauer et al.

(10) Patent No.: US 7,993,904 B2
(45) Date of Patent: Aug. 9, 2011

(54) PROCESS FOR THE PREPARATION OF OPTICALLY ACTIVE 5-SUBSTITUTED 2-OXAZOLIDINONES FROM RACEMIC EPOXIDES AND CYANATE EMPLOYING A HALOHYDRIN DEHALOGENASE

(75) Inventors: Bernhard Hauer, Fussgönheim (DE); Dirk Barend Janssen, Roden (NL); Maja Majeric Elenkov, Zagreb (HR)

(73) Assignee: BASF SE, Ludwigshafen (DE)

( * ) Notice: Subject to any disclaimer, the term of this patent is extended or adjusted under 35 U.S.C. 154(b) by 522 days.

(21) Appl. No.: 12/279,786

(22) PCT Filed: Feb. 28, 2007

(86) PCT No.: PCT/EP2007/051861
§ 371 (c)(1),
(2), (4) Date: Aug. 18, 2008

(87) PCT Pub. No.: WO2007/099107
PCT Pub. Date: Sep. 7, 2007

(65) Prior Publication Data
US 2009/0042261 A1    Feb. 12, 2009

(30) Foreign Application Priority Data

Mar. 3, 2006   (EP) .................................... 06110638

(51) Int. Cl.
*C12P 17/14*   (2006.01)
*C12P 41/00*   (2006.01)

(52) U.S. Cl. ....................................... 435/280; 435/120
(58) Field of Classification Search ....................... None
See application file for complete search history.

(56) References Cited

U.S. PATENT DOCUMENTS
2003/0124693 A1    7/2003   Spelberg et al.

FOREIGN PATENT DOCUMENTS
WO   WO-01/90397 A1    11/2001
WO   WO-2005/017141 A1   2/2005

OTHER PUBLICATIONS

Bertau, M., et al., "A Novel Highly Stereoselective Synthesis of Chiral 5- and 4,5-Substituted 2-Oxazolidinones", Tetrahedron: Asymmetry, 2001, vol. 12, pp. 2103-2107.
Lutje Spelberg, J. H., et al., "Exploration of the Biocatalytic Potential of a Halohydrin Dehalogenase using Chromogenic Substrates", Tetrahedron: Asymmetry, 2002, vol. 13, pp. 1083-1089.
Kasai, N., et al., "Chiral C3 Epoxides and Halohydrins: Their Preparation and Synthetic Application", Journal of Molecular Catalysis B: Enzymatic, 1998, vol. 4, pp. 237-252.
Nakamura, T., et al., "A New Catalytic Function of Halohydrin Hydrogen-Halide-Lyase, Synthesis of β-Hydroxynitriles from Epoxides and Cyanide", Biochemical and Biophysical Research Communications, 1991, vol. 180, No. 1, pp. 124-130.

*Primary Examiner* — Sandra Saucier
(74) *Attorney, Agent, or Firm* — Conolly Bove Lodge & Hutz LLP

(57) ABSTRACT

A process for the production of an optically enriched oxazolidinone of the formula (2a) or (2b), by reacting an epoxide of the formula (1) with cyanate in the presence of halo-hydrin dehalogenase.

4 Claims, No Drawings

SEQUENCE LISTING

```
<160> NUMBER OF SEQ ID NOS: 1

<210> SEQ ID NO 1
<211> LENGTH: 254
<212> TYPE: PRT
<213> ORGANISM: Agrobacterium radiobacter

<400> SEQUENCE: 1

Met Ser Thr Ala Ile Val Thr Asn Val Lys His Phe Gly Gly Met Gly
1               5                   10                  15

Ser Ala Leu Arg Leu Ser Glu Ala Gly His Thr Val Ala Cys His Asp
                20                  25                  30

Glu Ser Phe Lys Gln Lys Asp Glu Leu Glu Ala Phe Ala Glu Thr Tyr
            35                  40                  45

Pro Gln Leu Lys Pro Met Ser Glu Gln Glu Pro Ala Glu Leu Ile Glu
        50                  55                  60

Ala Val Thr Ser Ala Tyr Gly Gln Val Asp Val Leu Val Ser Asn Asp
65                  70                  75                  80

Ile Phe Ala Pro Glu Phe Gln Pro Ile Asp Lys Tyr Ala Val Glu Asp
                85                  90                  95

Tyr Arg Gly Ala Val Glu Ala Leu Gln Ile Arg Pro Phe Ala Leu Val
            100                 105                 110

Asn Ala Val Ala Ser Gln Met Lys Lys Arg Lys Ser Gly His Ile Ile
        115                 120                 125

Phe Ile Thr Ser Ala Thr Pro Phe Gly Pro Trp Lys Glu Leu Ser Thr
    130                 135                 140

Tyr Thr Ser Ala Arg Ala Gly Ala Cys Thr Leu Ala Asn Ala Leu Ser
145                 150                 155                 160

Lys Glu Leu Gly Glu Tyr Asn Ile Pro Val Phe Ala Ile Gly Pro Asn
                165                 170                 175

Tyr Leu His Ser Glu Asp Ser Pro Tyr Phe Tyr Pro Thr Glu Pro Trp
            180                 185                 190

Lys Thr Asn Pro Glu His Val Ala His Val Lys Lys Val Thr Ala Leu
        195                 200                 205

Gln Arg Leu Gly Thr Gln Lys Glu Leu Gly Glu Leu Val Ala Phe Leu
    210                 215                 220

Ala Ser Gly Ser Cys Asp Tyr Leu Thr Gly Gln Val Phe Trp Leu Ala
225                 230                 235                 240

Gly Gly Phe Pro Met Ile Glu Arg Trp Pro Gly Met Pro Glu
                245                 250
```

PROCESS FOR THE PREPARATION OF OPTICALLY ACTIVE 5-SUBSTITUTED 2-OXAZOLIDINONES FROM RACEMIC EPOXIDES AND CYANATE EMPLOYING A HALOHYDRIN DEHALOGENASE

RELATED APPLICATIONS

This application is a national stage application (under 35 U.S.C. §371) of PCT/EP2007/051861, filed Feb. 28, 2007, which claims benefit of European Application No. 06110638.1, filed Mar. 3, 2006.

FIELD OF THE INVENTION

The invention relates to a process for the production of an optically enriched oxazolidinones.

BACKGROUND OF THE INVENTION

Nakamura et al. (Biochem. Biophys. Res. Comm. 1991, Vol 180, No. 1, 124-130) describe a new catalytic function of halohydrin hydrogen-halide-Lyase for the synthesis of β-hydroxynitriles.

Spelberg et al. (Tetrahedron Asymmetry 2002, 13, 1083-1089) analyze the biocatalytic potential of a halohydrin dehalogenase from *Agrobacterium radiobacter*.

WO 2005/017141 discloses improved halohydrin dehalogenases and related polynucleotides.

US 2003/0124693A1 discloses the enzymatic conversion of epoxides.

WO 01/90397 discloses the enzymatic conversion of epoxides with different nucleophiles to the corresponding alcohols.

DETAILED DESCRIPTION OF THE INVENTION

The present invention provides a process for the production of an optically enriched oxazolidinones of the formula (2a) or (2b), by reacting an epoxide of the formula (1) with a cyanate in the presence of halohydrin dehalogenase.

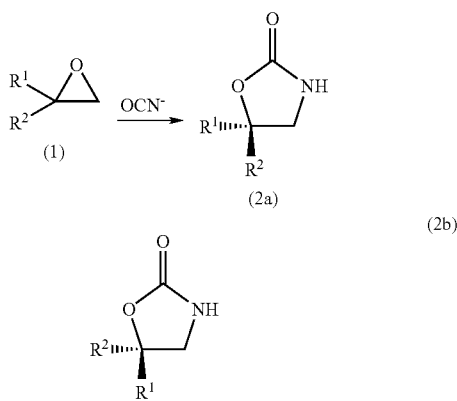

wherein R1 and R2 are chosen independent from each other from hydrogen, optionally substituted alkyl groups, aryl groups, aralkyl groups, alkenyl groups, cycloalkyl groups with the proviso R1≠R2, and recovering the optically enriched oxazolidinone.

The enzyme used is a halohydrin dehalogenase. A highly suitable halohydrin dehalogenase is a polypeptide having an amino acid sequence as shown in the Sequence Listing (SEQ ID NO: 1) or a homologue or functional derivative thereof. In the context of the invention, the term 'a homologue' refers to a sequence which is at least for 90% homologous, and preferably at least 90% identical, to the sequence of which it is a homologue. A functional derivative is a polypeptide which has undergone a minor derivatization or modification substantially without adversely affecting the enzymatic and catalytic properties of the polypeptide. Suitable examples of enzymes that can be used are halohydrin dehalogenase of *Agrobacterium radiobacter* (CBS 750.97), *Mycobacterium* sp. strain GP1 (Poelarends et al J. Bacteriol., 1999, 181, 2050) or *Arthrobacter* sp. strain AD2 (van den Wijngaard et al., J. Bacteriol., 1991, 124).

Particular good results have been obtained using a halohydrin dehalogenase derived from *Agrobacterium radiobacter* strain AD1 (HheC) deposited at the Centraal Bureau voor de Schimmelcultures on May 7, 1997 under deposit number CBS 750.97. Another enzyme obtained from this organism has been described extensively in the international patent application WO 98/53081 for its epoxide hydrolase activity.

It is to be noted that an enzyme used according to the invention, a halohydrin dehalogenase, should be distinguished from epoxide hydrolases. The latter have been described extensively in Archer, Tetrahedron, 53 (1997), pp. 15617-15662. The only feature that both types of enzymes may have in common is that they can be isolated from *Agrobacterium radiobacter* strain AD1. Likewise, Lutje Spelberg et al., Tetrahedron: Asymmetry, 9 (1998), pp. 459-466 and European patent application EP 0 879 890 relate to applications of an epoxide hydrolase.

The activity under process conditions, stability, and enantioselectivity of the halohydrin dehalogenasae can be improved by methods known in the field, including site-directed mutagenesis to remove labile groups and to modify the enantioselectivity, directed evolution employing gene shuffling, site-saturation mutagenesis, or structure-inspired random mutagenesis, or error prone PCR. These methods are known in the field (Powell et al., 2001, ACIE 40, 3948; Otten and Quax, 2005, Biomol. Eng. 22, 1; Williams et al., 2004, Cell Mol Life Sci 61:3034). Such mutagenesis methods are applicable for improving halohydrin dehalogenase performance as was recently shown by the construction of mutants with increased activity and enantioselectivity (Tang et al., 2005, Biochemistry 44, 6609; Tang et al., 2003, Biochemistry 42, 14057) and of mutants with improved stability (Tang et al., 2002, Enz Microb Techn. 30, 251).

Improved halohydrin dehalogenases are disclosed eg. in WO 2005/018579 A2 and WO 2005/017141 A1.). The mutations that were introduced include replacements of Cys by Ser. Further improved halohydrin dehalogenases can be produced by introducing mutations into position 134 (Thr) of SEQ ID NO:1, especially substitutions such as replacement of Thr by Ala.

The enzyme can be added as whole cells, in lyophilized form as a crude extract or as a purified enzyme. The enzyme can be immobilized on a macroscopic carriers such as cellulose, sephadex or dextran. The enzyme can also be applied as crosslinked enzyme crystals (CLEC's) or entrapped in reversed micelles. In a typical experiment, an enzyme solution is mixed with a buffer solution containing a nucleophile and an epoxide. Optionally, additives such as mercapto ethanol or glycerol can be added to the reaction mixture to stabilize the enzyme.

The epoxide of the formula (1) can be prepared from corresponding ketone using sulfonium ylids, (Mosset, P.; Gree, R. *Syn. Comm.* 1985, 15, 749-757) or by oxidation of alkenes using peroxy-carboxylic acid such as m-CPBA (meta-chloroperoxybenzoic acid). (Schwartz, N. N.; Blumbergs, J. H. *J. Org. Chem.* 1964, 29, 1976-1979).

The R1 and R2 groups are independent from each other hydrogen, optionally substituted, aromatic or aliphatic groups, which preferably contains from 1 to 20, more preferred from 1 to 10 carbon atoms. Preferably, R1, and R2 are chosen from the group of hydrogen, optionally substituted alkyl, aryl, aralkyl, alkenyl, cycloalkyl, and alkoxy groups. An optically enriches tertiary oxazolidinone of the formula (2a) or (2b) can be produced by the process according to the invention only if R1 is chemically distinct from R2.

Preferred examples of the alkyl group represented by R1 or R2 include straight or branched alkyl groups having 1 to 15 carbon atoms such as a methyl group, ethyl group, propyl group, isopropyl group, butyl group, pentyl group, hexyl group, heptyl group or dodecyl group.

Further preferred residues are those where R1 and R2 are chosen from the group H, —$(CH_2)_n$—$CH_3$, with n=0 to n=8, —$C_6H_5$ (phenyl), —$(CH_2)_n$—$(C_6H)_5$ (arylalkyl) —$C_6H_{11}$ (cyclohexyl), $CH_2CO_2R^3$ and R3 is chosen from —$CH_3$ (methyl), —$C_2H_5$ (-ethyl), —$C(CH_3)_3$ (tert-butyl).

The alkyl group can have substituents such as a halogen atom, The alkyl group can have a substituent such as an hydroxyl group, for example glycidol. The alkyl group can have a unsubstituted or substituted amino group such as amino, methylamino or dimethylamino. Examples of aryl groups represented by R1 or R2 include phenyl and naphtyl groups. Styrene oxide derivatives having a substituent or multiple substituents on the aromatic ring are examples of the phenyl group. Representative examples of epoxides are styrene oxide, 4-nitrostyrene oxide, 2-nitrostyrene oxide, 3-nitrostyrene oxide, 3-chlorostyrene oxide, 4 chlorostyrene oxide or 2,3-dichlorostyrene oxide. Examples of aralkyl groups represented by R1 or R2 include a benzyl group, 2-phenylethyl group and a 1-naphtylmethyl group. Examples of alkenyl groups represented by R1 or R2 include a vinyl group, allyl group and 5-hexenyl group. Examples of cycloalkyl groups represented by R1 or R2 include a cyclopropyl group, cyclobutyl group, cyclopentyl group and cyclohexyl group. Examples of alkoxy groups represented by R1 or R2 include a phenoxy group, 4-nitrophenoxy group, napthyloxy group, methoxy group, hexyloxy group and vinyloxy group.

The epoxide (1) can be present in solubilized form in a concentration of 1 to 300 mM or as a second solid or liquid phase in concentration up to 300 mM in the reaction medium. The epoxide itself can be the second phase or it can be dissolved in a second organic phase. This can be done by dissolving the epoxide in an organic solvent which is immiscible with water, such as hexane or octane. The obtained solution is then brought into contact with the aqueous phase containing the enzyme and the two phases are vigorously mixed. The use of such a second phase has the advantage that the separation of the epoxide and the alcohol after the reaction can be simplified. Generally, the alcohol is expected to remain solubilized in the aqueous phase and the epoxide can typically be recovered from the organic phase. Preferably, the epoxide is prior to its conversion brought in an aqueous medium in which it will preferably be present in an amount of 0.01 to 20 wt. %, based on the combined weights of the aqueous medium and the epoxide.

It is preferred that the reaction is carried out in a buffered aqueous medium to which the epoxide (1) is solubilized or is added as a second solid or liquid phase. Suitable buffers are for example Tris-buffer (2 amino-2-(hydroxymethyl)-1,3 propanediol adjusted to a desired pH with $H_2SO_4$), glycine-buffer (glycine adjusted to a desired pH by NaOH), phosphates buffer or MOPS buffer (4-morpholinepropanesulfonic acid adjusted to a desired pH with NaOH). These are preferably used a concentration of 50 to 250 mM.

Optionally, co-solvents like dimethyl sulfoxide, tetrahydrofuran or acetonitrile may be added to increase the solubility of the epoxide (1). Co-solvents may be added in amounts of 5 vol. % up to 50 vol. %. An increasing percentage of co-solvent may favor the solubility of the epoxide (1). However, a disadvantageous inactivation of the enzyme can be observed at higher co-solvent concentrations.

The pH of the medium preferably lies between 3 and 12, more preferably between 6.5 and 8. The temperature at which the reaction is carried out preferably lies between 0 to 60° C., more preferably between 20 and 30° C.

The cyanate reacting in the process according to the invention is added preferably as alkali cyanate such as sodium or potassium cyanate.

After the reaction the whole reaction mixture can be extracted using organic solvents such as diethylether, ethyl acetate, dichloromethane or toluene. The epoxide enantiomer which do not react or only very slowly and the optically enriched oxazolidinone of the formula (2a) or (2b) can subsequently be separated by techniques such as crystallisation (in the case of solid substances), fraction distillation or flash chromatography e.g. on silica 60H using heptane/ethylacetate (ratio 7:3) as eluent or other separation techniques well-known in the art.

The enantiomeric composition of the epoxides and oxazolidinones (2a) or (2b) can be determined using chiral gaschromatography or chiral HPLC.

The separated optically enriched epoxides can be used for further synthetic steps, especially for a ring-opening with nucleophilic agents which allows the production of a substituted tertiary alcohol in an optically pure form.

The invention will now be further elucidated by the following, non-restrictive examples.

EXAMPLES

Example I 250 mMol of racemic 2-ethyloxirane (formula 1, R1=H; R2=Et) was dissolved in 500 mMol Tris-$SO_4$ buffer (pH 7.5), followed by addition of purified enzyme (1 wt % of halohydrin dehalogenase HheC in Tris buffer) and 125 mMol NaOCN. The reaction mixture was stirred at room temperature (24° C.) and monitored by gas chromatography (GC). The reaction was stopped after 24 h and extracted three times by adding ethylacetate. The combined organic phases were dried over $Na_2SO_4$ and evaporated. The crude product was chromatographed on a silica gel 60 H using pentane/$CH_2Cl_2$ (4:6) as eluent. This yielded 5R-5-ethyloxazolidin-2-on (35% yield, e.e. 82%). Optical purities were determined by GC using a Chiraldex G-TA column (30 m×0.25 mm×0.25 m). The NMR data were identical with those of synthesized racemic reference compounds.

Example II 250 mMol of racemic 2-ethyl-2-methyloxirane (formula 1, R1=Me; R2=Et) was dissolved in 500 mMol Tris-$SO_4$ buffer (pH 7.5), followed by addition of purified enzyme (1 wt % of halohydrin dehalogenase HheC in Tris buffer) and 125 mMol NaOCN. The reaction mixture was stirred at room temperature (24° C.) and monitored by gas chromatography (GC). The reaction was stopped after 7 h and extracted three times by adding ethylacetate. The combined organic phases were dried over $Na_2SO_4$ and evaporated. The crude product was chromatographed on a silica gel 60 H using pentane/$CH_2Cl_2$ (4:6) as eluent. This yielded 5R-5-ethyl-5-methyloxazolidin-2-on (40% yield, e.e. 97%). Optical purities were determined by GC using a Chiraldex G-TA column (30 m×0.25 mm×0.25 m). The NMR data were identical with those of synthesized racemic reference compounds.

The invention claimed is:

1. A process for producing an optically enriched oxazolidinone of formula (2a) or (2b) comprising reacting an epoxide of formula (1) with cyanate in the presence of a halohydrin dehalogenase

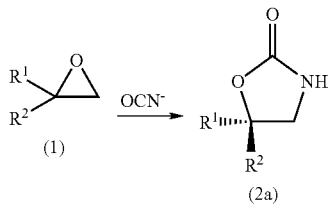

(1)

(2a)

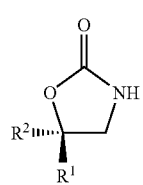

(2b)

wherein $R^1$ and $R^2$ are, independently, hydrogen, an optionally substituted alkyl group, an optionally substituted aryl group, an optionally substituted aralkyl group, an optionally substituted alkenyl group, or an optionally substituted cycloalkyl group, with the proviso that $R^1 \neq R^2$, and recovering said optically enriched oxazolidinone of formula (2a) or (2b).

2. The process of claim 1, wherein $R^1$ and $R^2$ are selected from the group consisting of H and $-(CH_2)_n-CH_3$ wherein n is an integer from 0 to 8.

3. The process of claim 1, wherein said halohydrin dehalogenase is a polypeptide having the amino acid sequence of SEQ ID NO: 1 or a homologue thereof which has a sequence identity of at least 90%.

4. The process of claim 1, wherein said reaction is performed at a temperature in the range of from 0 to 60° C.

* * * * *